(12) United States Patent
Belgardt et al.

(10) Patent No.: US 7,608,221 B2
(45) Date of Patent: Oct. 27, 2009

(54) MULTI CHANNEL METERING DEVICE

(75) Inventors: Herbert Belgardt, Hamburg (DE); Jens Wilmer, Ahrensburg (DE); Holger Link, Hamburg (DE)

(73) Assignee: Eppendorf AG, Hamburg (DE)

( * ) Notice: Subject to any disclaimer, the term of this patent is extended or adjusted under 35 U.S.C. 154(b) by 655 days.

(21) Appl. No.: 11/471,252

(22) Filed: Jun. 20, 2006

(65) Prior Publication Data
US 2007/0003445 A1 Jan. 4, 2007

(30) Foreign Application Priority Data
Jun. 29, 2005 (DE) .................. 10 2005 030 196

(51) Int. Cl.
*B01L 3/02* (2006.01)
(52) U.S. Cl. .................. 422/100; 73/863.32; 73/864; 73/864.01
(58) Field of Classification Search .......... 422/63–68.1, 422/100; 436/180; 73/863.32, 864
See application file for complete search history.

(56) References Cited

U.S. PATENT DOCUMENTS

| 3,444,742 | A | | 5/1969 | Ellis et al. .................. 73/425.6 |
| 4,695,430 | A | * | 9/1987 | Coville et al. .................. 422/65 |
| 6,006,800 | A | * | 12/1999 | Nakano ...................... 141/130 |
| 6,143,252 | A | * | 11/2000 | Haxo et al. .................... 506/40 |
| 6,199,435 | B1 | * | 3/2001 | Wilmer et al. ............ 73/864.14 |
| 6,506,611 | B2 | * | 1/2003 | Bienert et al. ................ 436/180 |
| 7,344,048 | B2 | * | 3/2008 | Ueda et al. ...................... 221/4 |
| 2002/0176801 | A1 | * | 11/2002 | Giebeler et al. .......... 422/82.05 |
| 2004/0047765 | A1 | * | 3/2004 | Gordon et al. ................ 422/63 |
| 2007/0003445 | A1 | * | 1/2007 | Belgardt et al. ............. 422/100 |

FOREIGN PATENT DOCUMENTS

| CH | 671 526 | | 9/1989 |
| DE | 298 06 459 | U1 | 8/1998 |
| DE | 199 62 689 | A1 | 7/2001 |
| DE | 200 06 547 | U1 | 9/2001 |
| EP | 0 855 033 | B1 | 10/1996 |
| GB | 2 205 400 | A | 12/1988 |

OTHER PUBLICATIONS

Patent Abstract of Japan for Application No. 2000123338, filed Mar. 22, 2000.

* cited by examiner

*Primary Examiner*—Brian R. Gordon
(74) *Attorney, Agent, or Firm*—Vidas, Arrett & Steinkraus, P.A.

(57) ABSTRACT

Multi-channel metering device with displacement devices for displacing a plurality of air columns, a plurality of holders which comprise a shank for releasable connection to a pipette tip, a connector and a connecting channel extending from the free end of the shank to the connector, flexible pipes which connect the displacement devices to the connectors, a guide on which the holders may be displaced with shanks aligned parallel to one another and perpendicular to the guide, abutment surfaces on the faces of the holders facing one another, pins projecting from the holders, oriented perpendicular to the guide and the shanks, round chain links arranged on the pins of adjacent holders, a free space existing between the pins and the rounded portions of the round chain links when the abutment surfaces of the adjacent holders bear against one another, and a drive device which engages at least one of the two outer holders and by means of which the holders may be pushed apart and pushed together along the guide.

16 Claims, 3 Drawing Sheets

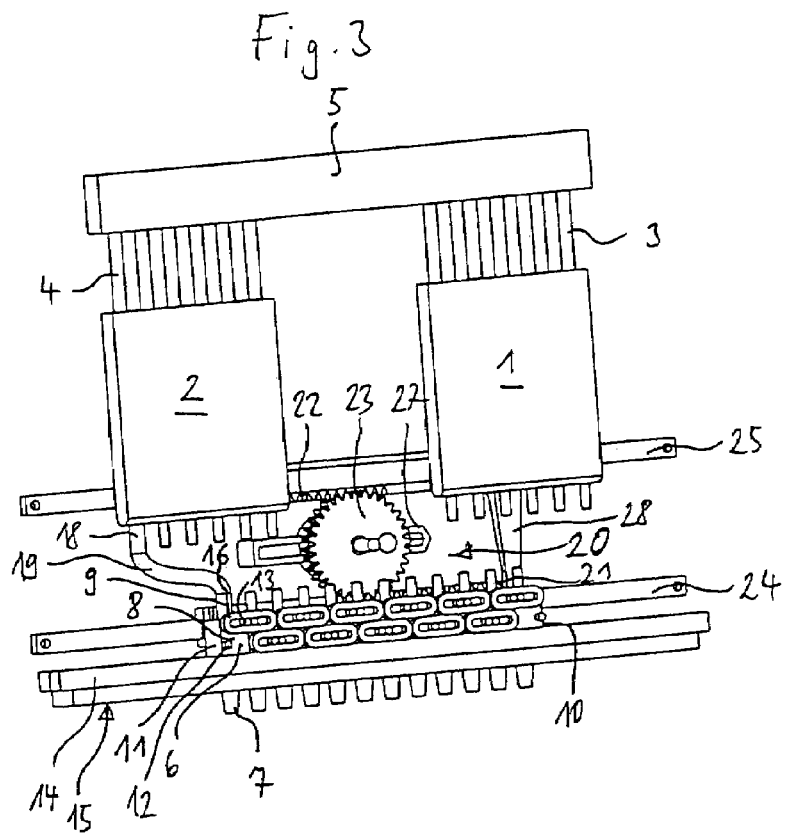
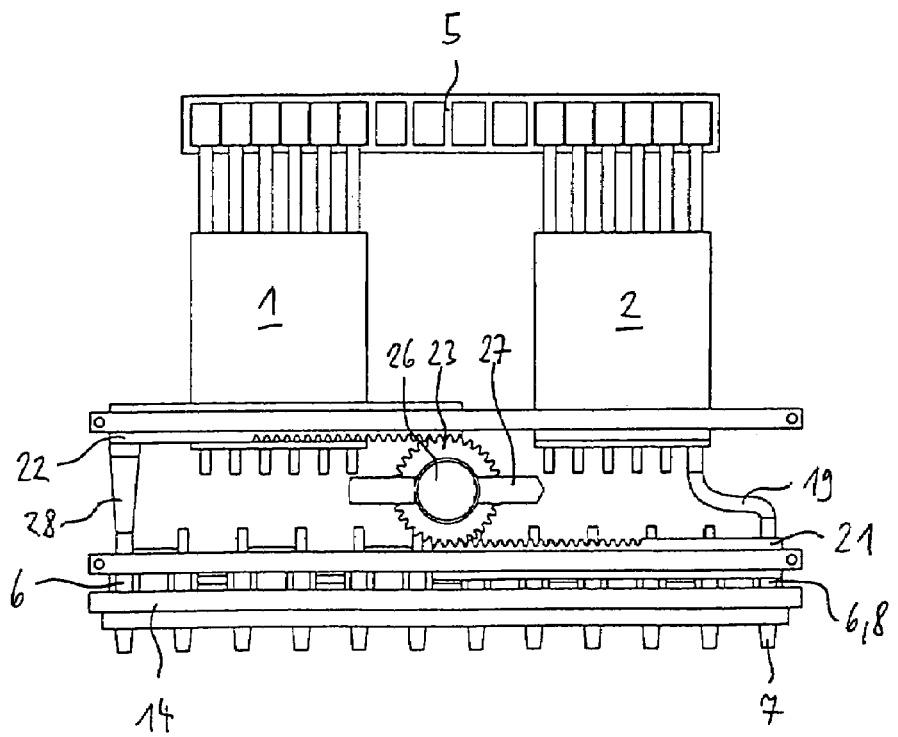

MULTI CHANNEL METERING DEVICE

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

Multi-channel metering devices are used, in particular in the laboratory, for simultaneously metering a plurality of liquid samples. The liquid samples are drawn in from a row of wells of a microtiter plate or other containers in pipette tips releasably attached to the multi-channel metering device or dispensed from the pipette tips into the containers. Multi-channel metering devices have holders with a shank, onto which pipette tips may be clamped. Displacement devices are present for suctioning the liquid samples into the pipette tips and expelling said liquid samples from the pipette tips, and which are able to displace air columns. They are generally designed as a piston-cylinder unit with a cylinder and a piston which is displaceable therein. The displacement devices are connected to apertures in the ends of the shanks via pipes and/or channels and on which the pipette tips are located. After the metering of the liquid samples the pipette tips may be forced off the shanks by means of a throw-off device. Fresh pipette tips may be mounted onto the shanks for further metering. As a result, carry-over between different liquid samples and contamination of the liquid samples and the multi-channel metering device are avoided.

Microtiter plates with 96 wells and a spacing from well to well of 9.0 mm are very common. Microtiter plates with 384 wells and a spacing from well to well of 4.5 mm are also very common. Multi-channel metering devices with rigidly arranged holders can only remove liquid samples from all the wells in a row and dispense liquid samples into said wells with one of the two types of plate. However, multi-channel metering devices are also already known in which the spacings of the holders may be adjusted to the different spacings of the wells. Thus, adjusting the holders by means of a pivotable slide rail for pins fixed to the holders (GB 2 205 400 A), the entire contents of which is hereby incorporated by reference in its entirety, and adjusting the holders via a scissor lever mechanism (EP 0 855 033 B1) the entire contents of which is hereby incorporated by reference in its entirety, are known. The known multi-channel metering devices with adjustable holders are indeed reliable but very costly in terms of construction.

Proceeding therefrom, the object of the invention is to propose a multi-channel metering device with a less costly but nevertheless reliable adjustment of the holders.

BRIEF SUMMARY OF THE INVENTION

The multi-channel metering device according to the invention has displacement devices for displacing a plurality of air columns, a plurality of holders which comprise a shank for releasable connection to a pipette tip, a connector and a connecting channel extending from the free end of the shank to the connector, flexible pipes which connect the displacement devices to the connectors, a guide on which the holders may be displaced with shanks aligned parallel to one another and perpendicular to the guide, abutment surfaces on the faces of the holders facing one another, pins projecting from the holders, oriented perpendicular to the guide and the shanks, round chain links arranged on the pins of adjacent holders, a free space existing between the pins and the rounded portions of the round chain links when the abutment surfaces of the adjacent holders bear against one another, and a drive device which engages at least one of the two outer holders and by means of which the holders may be pushed apart and pushed together along the guide.

In the multi-channel metering device according to the invention the holders are coupled with one another via round chain links. If the holders are pushed together so that their abutment surfaces bear against one another, the pins of adjacent holders within the round chain links connecting said adjacent holders are pushed together maximally, so that one respective free space exists between the pins and the rounded portions at the ends of the round chain links. If the holders are pulled apart maximally, the pins bear on the inside against the end face of the rounded portions of the round chain links. Thus the ability of the holders to be pushed together by the abutment surfaces bearing against one another and the ability of the holders to be pulled apart is determined by the bearing of the pins against the rounded portions of the round chain links. The two end positions are reliably and therefore permanently secured, so that when the holders are pushed together the shanks have a specific narrow spacing from one another and when the holders are pulled apart, the shanks have a specific wide spacing from one another. Referring to current conventional microtiter plates, the narrow spacing is, for example, 4.5 mm and the wide spacing 9.0 mm. The coupling of the holders via round chain links may be easily manufactured. The drive device may also be produced at low cost, as it only has to displace the two outer holders or only one thereof, preferably the other being secured. The round chain links are, for example, designed in the manner of the chain links of a round link chain which have a substantially oval body with a central, elongate aperture. Such round chain links are shown in the embodiment (see below). Apart from these round chain links in the actual sense, within the term round chain links, the invention includes chain links which are of tab-shaped design and in which the pins are arranged in two separate slots aligned toward one another, so that they may only be pushed together until they bear against the connecting region between the two slots. Chain links are also included which have a bearing eye for one of the adjacent pins and a slot for the other of the adjacent pins. In such embodiments, only the pin guided in the slot is displaceable if the holders are pushed together or pulled apart.

The pipette tips may be releasably connected to the shanks in various ways, for example by pressing or screwing on. Preferably the pipette tips are slipped on. To this end, according to an embodiment the shanks have a tapered end.

The guide may be designed in various ways. According to an embodiment the guide is formed from a guide body with a slot which is penetrated by the holders.

According to an embodiment the holders have a rectangular parallelepiped portion which comprises the shank on the lower face, the connector on the upper face, the abutment surfaces on the left and right face and the pins on the front face and/or rear face.

According to a further embodiment, the shank is passed through the slot of the guide body and the rectangular parallelepiped portion is located with the lower face on the upper face of the guide body.

Various embodiments of connectors are included for the flexible pipes. According to a preferred embodiment, the connectors are tube connections onto which the flexible pipes are clamped. Accordingly, further connectors may be designed on the displacement devices for the other ends of the flexible pipes.

According to a further embodiment, the two pins project from the front faces or rear faces of the rectangular parallelepiped portion, the two pins on each rectangular parallelepiped portion being offset in height, the pins connected via round chain links having the same height and adjacent round chain links able to be partially pushed over one another when the holders are pushed together.

The drive device may be configured in various ways. According to an embodiment, it comprises at least one toothed rack which engages one of the two outer holders and of which the toothing meshes with the toothing of a gear. According to a further embodiment, the drive device comprises two toothed racks, each of which engaging one of the two outer holders and the toothings of which meshing with the toothing of the gear, on different faces of the gear. By rotating the gear in different directions, the toothed racks and the holders connected thereto are moved toward one another or away from one another.

According to an embodiment, the gear is coupled with a rotary knob for manual operation. According to a further embodiment, the rotary knob is connected fixedly in rotation to the gear.

According to a further embodiment, the gear is coupled with, for example, an electric drive motor. According to a further embodiment the gear is coupled with the shaft of a drive motor via a pinion. Moreover, embodiments are included which comprise both a rotary knob for manual operation and a drive motor for motorised operation.

According to an embodiment, magnetic and/or latching devices are present for fixing the holders in the final positions. The magnetic and/or latching connections may cooperate directly with the holders or with elements of the drive device.

According to a preferred embodiment, the displacement devices have a plurality of parallel piston-cylinder devices with a cylinder and a longitudinally displaceable piston arranged therein, each cylinder being connected via a flexible pipe to a connector. According to a further embodiment the pistons are connected to at least one further drive device. The further drive device is, for example, a manual drive device. It is preferably driven by a motor.

BRIEF DESCRIPTION OF THE SEVERAL VIEWS OF THE DRAWINGS

The invention will be described in more detail hereinafter with reference to the accompanying drawings of an embodiment, in which:

FIG. 3 is an angled perspective view from the rear of the same device with the holders pushed together;

FIG. 4 is a front view of the same device with the holders pushed apart;

DETAILED DESCRIPTION OF THE INVENTION

Figure 1:
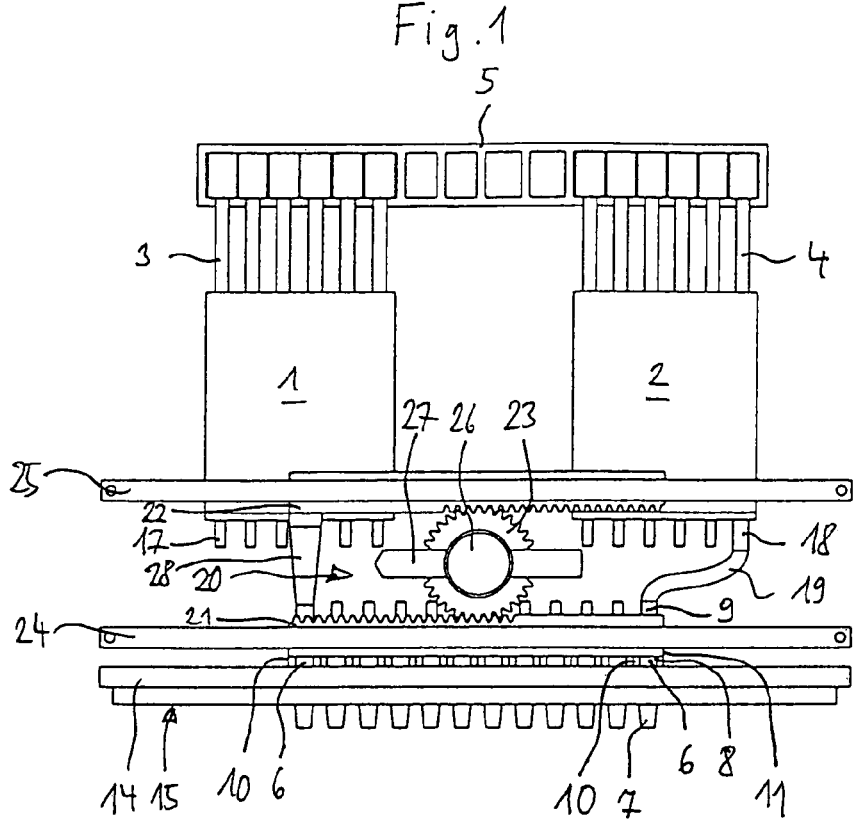
FIG. 1 is a front view of a manual multi-channel metering device (hereinafter 'device') with the holders pushed together.

While this invention may be embodied in many different forms, there are described in detail herein a specific preferred embodiment of the invention. This description is an exemplification of the principles of the invention and is not intended to limit the invention to the particular embodiment illustrated In the following description, the terms 'upper', 'lower', 'left' and 'right' refer to the arrangement of the device according to the drawings which corresponds to the conventional arrangement when using the device.

The device has displacement devices 1, 2 for displacing a plurality of air columns, which respectively comprise a plurality of cylinders, not shown, in a block and pistons which are displaceable therein. Piston rods 3, 4 for operating the pistons are guided out of the displacement devices 1, 2 and may be connected to a common drive (not shown) via a cross member 5.

Moreover, the device has a plurality of holders 6 (12 in the example). Each holder comprises a tapered shank 7 which projects downwards from the lower face of a substantially rectangular parallelepiped portion 8. Moreover, it comprises a tube connection 9 which projects upwards from the upper face of the rectangular parallelepiped portion 8. Each rectangular parallelepiped portion 8 has an abutment surface 10 on the left face (in FIGS. 1 and 4) and an abutment surface 11 on the right face (in FIGS. 1 and 4). Moreover, on the rear face each rectangular parallelepiped portion 8 has two pins 12, 13 projecting perpendicular thereto which are offset laterally and in height.

Moreover, a strip-shaped guide body 14 is present which in the longitudinal direction comprises a slot 15 extending from the upper to the lower face and which is not visible in the drawings. The slot 15 is closed at the two ends of the guide body 14.

The holders 6 are passed through the slot 15 with their tapered shanks and are located with the lower face of their rectangular parallelepiped portions 8 on the upper face of the guide body 14. The shanks 7 project from the lower face of the guide body 14. Moreover, left and right faces of rectangular parallelepiped portions 8 of adjacent holders 6 always face one another so that different abutment surfaces 10, 11 are oriented toward one another. The pins 12, 13 of adjacent holders 6 arranged adjacent to one another are always arranged at the same height.

Adjacent holders 6 are respectively connected to one another by a round chain link 16 which is located on adjacent pins 12 or 13 of the same height.

The displacement devices 1, 2 have further tube connections 17, 18 projecting downwards of which each communicates with a cylinder.

Each further tube connection 17, 18 is connected to a tube connection 9 of a holder 6 via a flexible tube 19. In the figures, only one respective flexible tube 19 is shown.

Moreover, a drive device 20 is present which comprises a lower toothed rack 21, an upper toothed rack 22 and a gear 23. The toothed racks 21, 22 are aligned parallel to the guide body 14. The lower toothed rack 21 is guided on a lower guide rail 24 and the upper toothed rack 22 on an upper guide rail 25.

The gear 23 is rotatably arranged between the toothed racks 21, 22. Its toothing meshes below with the toothing of the lower toothed rack 21 and above with the toothing of the upper toothed rack 22.

Moreover, the gear 23 is connected fixedly in rotation to a rotary knob 26 and a pointer 27 for manual operation.

The lower toothed rack 21 is fixedly connected to the right outer holder 6 (in FIGS. 1 and 4). The upper toothed rack 22 is fixedly connected via a projection 28 to the left outer holder 6 (in FIGS. 1 and 4).

The guide rails 24, 25, the guide body 14, the mounting of the gear 23 and the displacement devices 1, 2 are fastened to a support device (for example to a frame and/or in a housing).

Figure 2:
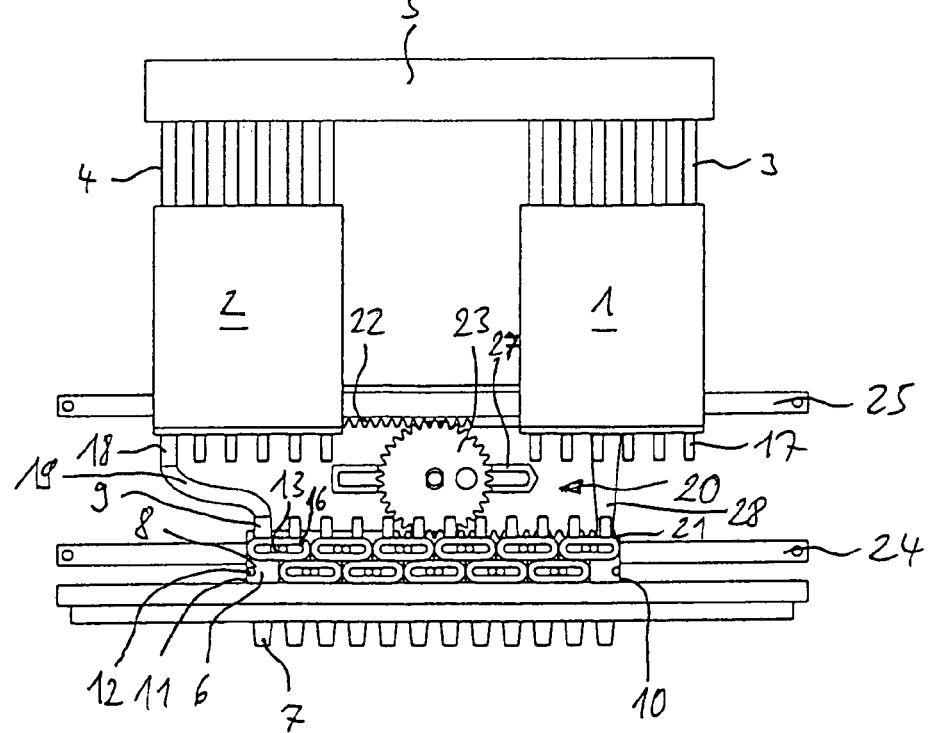
FIG. 2 is a rear view of the same device with the holders pushed together.

During use, the spacing of the shanks 7 is adjusted to the spacing of the wells of the respective microtiter plate used. By rotating the rotary knob 26 anti-clockwise (in FIGS. 1 and 4) the upper and lower toothed racks 21, 22 are substantially pushed over one another and thus the two outer holders 6 pushed toward one another. The holders 6 located therebetween are pushed together via the abutment surfaces 10, 11. In FIGS. 1 to 3 the device is shown in the situation in which the shanks 7 are pushed together with the smallest possible spacing (of, for example, 4.5 mm).

Figure 5:
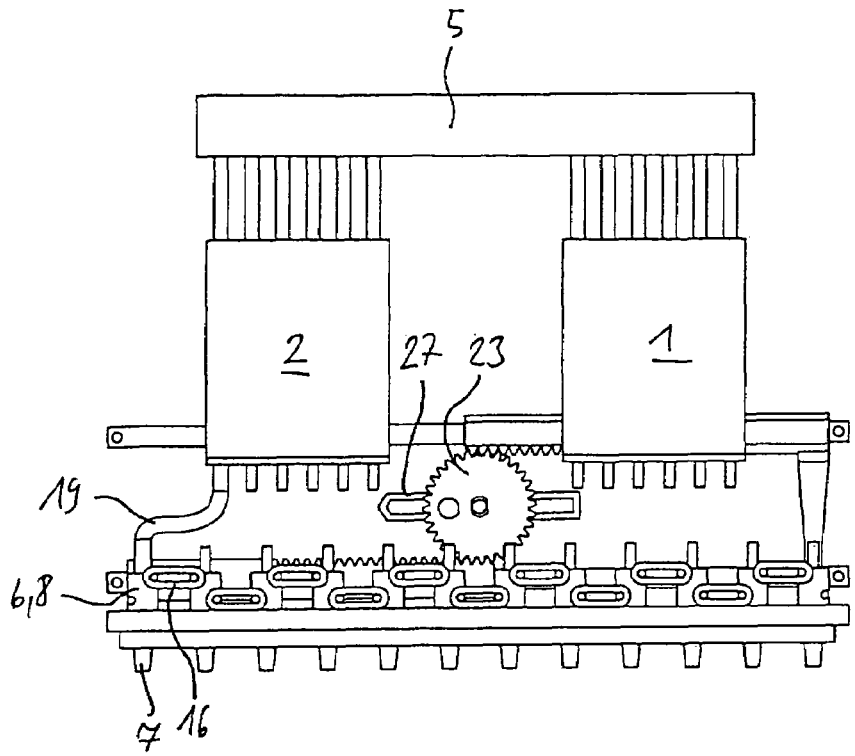
FIG. 5 is a rear view of the same device with the holders pushed apart.
Figure 6:
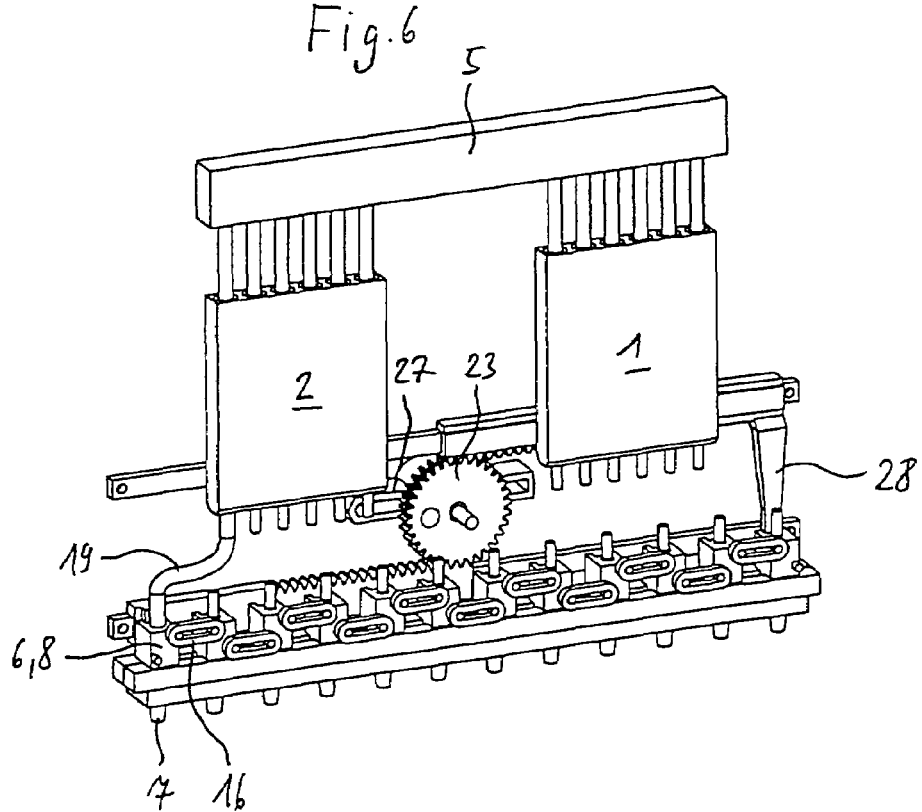
FIG. 6 is an angled perspective view of the same device with the holders pushed apart.

By rotating the rotary knob 26 clockwise (in FIGS. 1 and 4) the toothed racks 21, 22 are displaced toward different sides. As a result, the two outer holders 6 are moved apart and the holders 6 located therebetween are pulled apart as far as possible via the round chain links 16. This situation is shown in FIGS. 4 to 6. In this arrangement, the shanks 7 are maximally spaced apart from one another (for example 9.0 mm).

For metering liquids, pipette tips are mounted onto the shanks 7. By operating the displacement devices 1, 2 it is possible to draw in liquid from the wells of a microtiter plate into the pipette tips and/or to expel liquid from the pipette tips into the wells of a microtiter plate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. Multi-channel metering device comprising displacement devices (1, 2) for displacing a plurality of air columns, a plurality of holders (6) each which comprises a shank (7) for releasable connection to a pipette tip, a connector (9) and a connecting channel extending from a free end of the shank (7) to the connector (9), flexible pipes (19) which connect the displacement devices (1, 2) to the connectors (9), a guide (14) on which the holders (6) may be displaced with shanks (7) aligned parallel to one another and perpendicular to the guide (14), abutment surfaces (10, 11) on the faces of the holders (6) facing one another, two pins (12, 13) projecting from the holders (6), oriented perpendicular to the guide (14) and the shanks (7), round chain links (16) arranged on the pins (12, 13) of adjacent holders (6), a free space existing between the pins (12, 13) and the rounded portions of the round chain links (16), when the abutment surfaces (10, 11) of the adjacent holders (6) bear against one another, and a drive device (20) which engages at least one of two outer holders (6) and by means of which the holders (6) may be pushed apart and pushed together along the guide (14).

2. Multi-channel metering device according to claim 1, wherein the shanks (7) have a tapered end for mounting a pipette tip.

3. Multi-channel metering device according to claim 1, wherein the guide comprises a guide body (14) with a slot (15) which is penetrated by the holders (6).

4. Multi-channel metering device according to claim 1, wherein the holders (6) have a rectangular parallelepiped portion (8) which comprises the shank (7) on a lower face, the connector (9) on a upper face, the abutment surfaces (10, 11) on a left and right face and the pins (12, 13) on a front face and/or rear face.

5. Multi-channel metering device according to claim 1, wherein the shank (7) is passed through the slot (15) of the guide body (14) and the rectangular parallelepiped portion (8) is located with the lower face on the upper face of the guide body (14).

6. Multi-channel metering device according to claim 1, wherein the connectors are tube connections (9) onto which the flexible pipes (19) are clamped.

7. Multi-channel metering device according to claim 4, in which wherein the two pins (12, 13) project from the front faces or rear faces of the rectangular parallelepiped portion (8), the two pins (12, 13) on each rectangular parallelepiped portion (8) being offset in height, the pins (12, 13) connected via round chain links (16) having the same height, and adjacent round chain links (16) able to be partially pushed over one another when the holders (6) are pushed together.

8. Multi-channel metering device according to claim 1, wherein the drive device (20) comprises at least one toothed rack (21, 22) which engages one of the two outer holders (6) and of which the toothing meshes with the toothing of a gear (23).

9. Multi-channel metering device according to claim 8, wherein the drive device (20) comprises two toothed racks (21, 22), each of which engaging one of the two outer holders (6) and the toothings of which meshing with the toothing of the gear (23), on different faces of the gear (23).

10. Multi-channel metering device according to claim 8, wherein the gear (23) is coupled with a rotary knob (26) for manual operation.

11. Multi-channel metering device according to claim 10, wherein the rotary knob (26) is connected fixedly in rotation to the gear (23).

12. Multi-channel metering device according to claim 8, wherein the gear (23) is coupled with an electric drive motor.

13. Multi-channel metering device according to claim 12, wherein the gear (23) is coupled with the shaft of the drive motor via a pinion.

14. Multi-channel metering device according to claim 1, which comprises magnetic and/or latching devices for fixing the holders (6) in a final positions.

15. Multi-channel metering device according to claim 1, wherein the displacement devices (1, 2) have a plurality of parallel piston-cylinder devices with a cylinder and a longitudinally displaceable piston arranged therein, each cylinder being connected via a flexible pipe (19) to a connector (9).

16. Multi-channel metering device according to claim 15, wherein the pistons are connected to at least one further drive device.

* * * * *